United States Patent [19]
Johns

[11] 3,992,238
[45] Nov. 16, 1976

[54] METHOD FOR MOLDING A PROTECTIVE PAD

[75] Inventor: Herman S. Johns, Gastonia, N.C.

[73] Assignee: Medical Specialties, Inc., Charlotte, N.C.

[22] Filed: Mar. 31, 1975

[21] Appl. No.: 563,585

[52] U.S. Cl. ................................ 156/93; 156/245; 156/285; 264/45.1; 264/46.4; 264/91; 264/112; 264/234; 264/257; 264/259; 264/261; 264/DIG. 7

[51] Int. Cl.² ................ B29C 29/00; B29D 9/00

[58] Field of Search ............... 128/90, 89 R, 80 R, 128/80 H; 264/46.4, 46.5, DIG. 7, 90, 54, 91, 101, 250, 275, 277, 347, 261, 258, 263, 236, 255, 265, 126, 45.4, 45.1, 257, 232, 234; 156/91, 92, 93, 245, 276, 285

[56] References Cited
UNITED STATES PATENTS

| | | | |
|---|---|---|---|
| 2,060,001 | 11/1936 | Attwood et al. | 128/89 R |
| 2,927,876 | 3/1960 | Hoppe et al. | 264/46.5 |
| 2,997,739 | 8/1961 | Smith et al. | 264/347 |
| 3,015,851 | 1/1962 | Wiles | 264/101 |
| 3,086,248 | 4/1963 | Culp | 264/101 |
| 3,177,275 | 4/1965 | Brenner | 264/91 |
| 3,193,440 | 7/1965 | Schafer | 264/DIG. 7 |
| 3,207,822 | 9/1965 | Makowski | 264/275 |
| 3,298,365 | 1/1967 | Lewis | 128/80 R |
| 3,318,305 | 5/1967 | Schultz | 128/80 R |
| 3,401,128 | 9/1968 | Terry | 264/DIG. 7 |
| 3,452,124 | 6/1969 | Knapp | 264/102 |
| 3,585,639 | 6/1971 | Enicks | 128/90 |
| 3,878,277 | 4/1975 | Velte | 264/46.4 |

FOREIGN PATENTS OR APPLICATIONS

| | | | |
|---|---|---|---|
| 664,192 | 6/1963 | Canada | 264/54 |

*Primary Examiner*—Willard E. Hoag
*Attorney, Agent, or Firm*—Bell, Seltzer, Park & Gibson

[57] ABSTRACT

A method for molding a protective pad or the like, and which includes a convex mold surface having a plurality of perforations therethrough, and a cooperating concave mold surface also having a plurality of perforations therethrough. The two mold surfaces are mounted for relative movement with respect to each other and such that the concave mold surface initially faces upwardly to receive the molding material therein, and then is inverted and translated downwardly into face to face relationship with the convex mold surface. The apparatus includes a vacuum system for drawing a partial vacuum beneath the concave mold surface to maintain a predetermined distribution of molding material on the concave mold surface during the movement thereof, and means is provided for introducing steam into the mold cavity to cure the molding material.

13 Claims, 11 Drawing Figures

METHOD FOR MOLDING A PROTECTIVE PAD

The present invention relates to a method for molding a protective foam pad adapted to be positioned on an elbow or heel of a patient, and characterized by a generally circular outline and a generally converging concavo-convex cross-sectional configuration.

In molding foam products of generally rectangular cross section, such as the cervical collar illustrated in the patent to Gaylord, U.S. Pat. No. 3,696,810, it is conventional to employ mating mold segments fabricated from perforated sheet metal and which are adapted to be positioned in a spaced apart, face to face relationship to define a mold cavity having the desired configuration. Typically, one mold segment is initially filled with a relatively dry, particulate foam material having an adhesive mixed therewith. The mold segments are then closed, and steam is introduced into the mold cavity through the perforations to thereby cure the adhesive and form the finished product.

While the above process is satisfactory for many foam products of uncomplicated shape, it has been found to be unsatisfactory for molding a more complex product. For example, the copending application of John F. Gaylord, Ser. No. 492,890, now U.S. Pat. No. 3,937,218 and having a common assignee with the present application, discloses a protective pad of circular outline and which has a generally converging concavo-convex cross-sectional configuration. Such pads are not able to be satisfactorily molded by the above described process since difficulties are encountered in maintaining the desired distribution of the molding material on the mold surfaces during the molding operation. More particularly, when the molding material is placed in the concave mold and the convex mold is brought into operative engagement therewith, the movement of the convex mold into the concave mold tends to drag the molding material laterally along the wall of the concave mold and into the center thereof. Thus the peripheral edges of the resulting product have insufficient foam material, while the center has excess material and is unduly dense. As a result, the peripheral edges of the resulting product lack sufficient integrity to permit the sewing of a binder or the like thereabout, and the hard, dense center may be irritating to the wearer.

Difficulties are also encountered in the prior molding process in attempting to enclose the molded foam product in a suitable fabric covering. As will be apparent, the covering will normally separate from the concave surface of the product, resulting in a baggy appearance. To attempt to adhesively adhere the fabric to this surface is a time consuming and thus expensive operation, and it is difficult to achieve a smooth, uniform appearance.

It is accordingly an object of the present invention to provide a method and apparatus for molding a protective pad of generally arcuate cross-sectional configuration, and which overcomes the above noted problems associated with the present molding procedures.

It is a more particular object of the present invention to provide a method and apparatus for molding a protective pad wherein the distribution of the molding material within the mold cavity may be accurately determined and controlled, thereby permitting accurate control of the density in all portions of the resulting product.

It is still another object of the present invention to provide a method and apparatus for molding a protective pad and wherein a fabric material is simultaneously secured in a smooth and uniform manner to each face of the molded product during the molding operation.

These and other objects and advantages of the present invention are achieved in the embodiment illustrated herein by the provision of an apparatus which comprises a male mold canister having a generally convex mold surface, a female mold canister having a generally concave mold surface, and means for mounting the male and female canisters for movement relative to each other and between a non-operative position wherein the canisters are separated and the concave mold surface faces upwardly to permit receipt of the material to be molded therewithin, and an operative position wherein the concave and convex mold surfaces are in spaced apart, face to face relationship to define a mold cavity therebetween. The concave mold surface includes a plurality of relatively small perforations distributed over the area thereof, and means are provided for selectively drawing a partial vacuum within the female mold canister such that the vacuum acts through the perforations to maintain a predetermined distribution of the material to be molded within the concave mold surface during the transfer of the canisters into their operative position.

The convex mold surface of the male mold canister may also include a plurality of perforations, and the apparatus may further comprise means for introducing steam into the interior of the male mold canister such that the steam passes through the perforations in the convex and concave mold surfaces and thus through the mold cavity to thereby heat the material positioned therewithin. The method of the present invention may also incorporate the positioning of fabric segments over each of the concave and convex mold surfaces such that the fabric segments overlie the opposite faces of the resulting product and are adhered thereto.

Some of the objects and advantages of the invention having been stated, others will appear as the description proceeds when taken in connection with the accompanying drawings, in which.

Figures 8, 9, 10, 11:
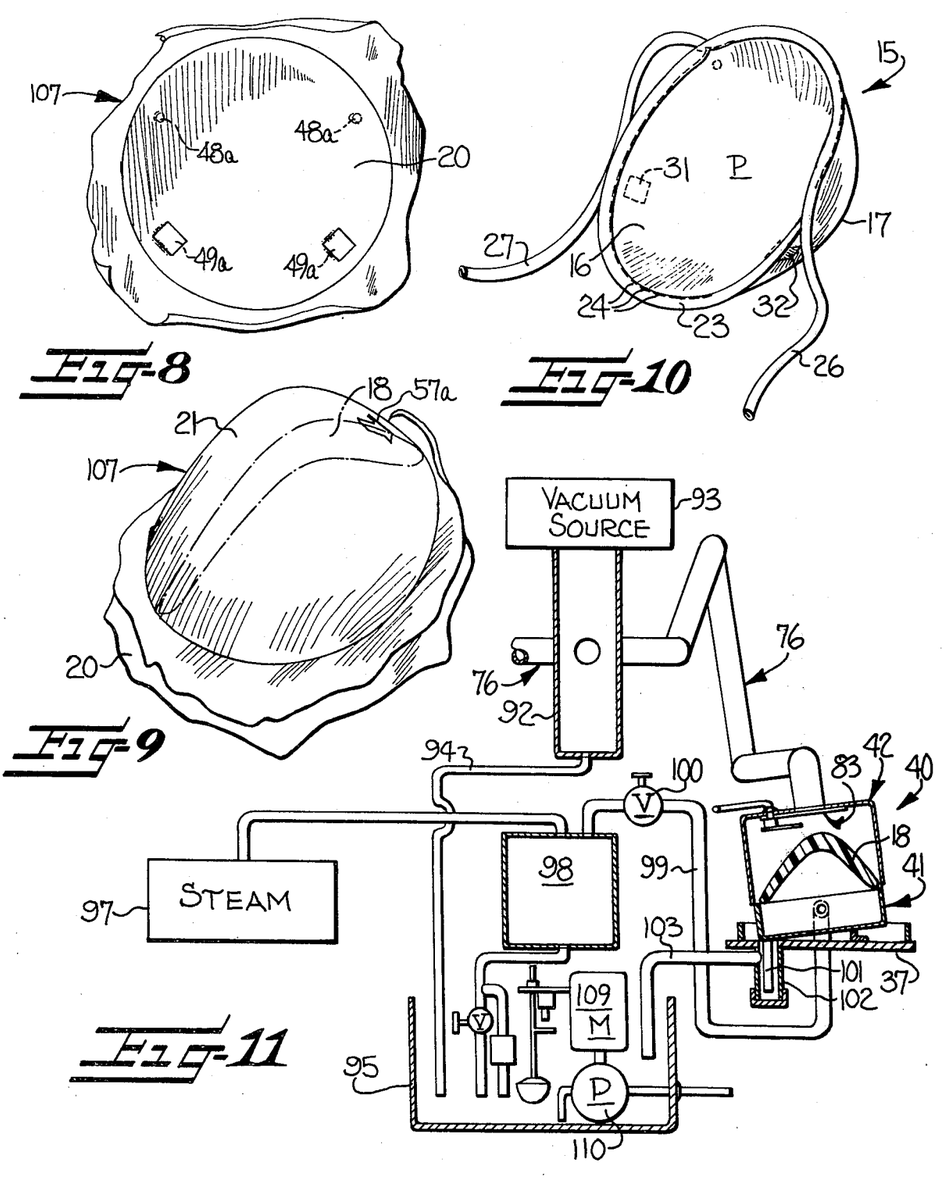
FIG. 8 is a front elevation view of a protective pad produced in accordance with the present invention, and prior to the final finishing operations.
FIG. 9 is a perspective view of the opposite side of the pad shown in FIG. 8.
FIG. 10 is a perspective view of the pad shown in FIGS. 8 and 9 after the finishing operations.
FIG. 11 is a schematic sectional view illustrating the vacuum and steam systems of the apparatus shown in FIG. 1.

Referring more specifically to the drawings, a protective pad adapted to be molded by the present invention is illustrated generally at 15 in FIG. 10. As illustrated, the pad has a generally circular outline, and a generally arcuate, converging concavo-convex cross-sectional configuration as seen in dashed lines in FIG. 9. The pad 15 thereby defines a curved, somewhat scoop-like shape having a concave inner surface 16 defining a pocket P adapted to receive the heel or elbow of a wearer therein, and a convex outer surface 17. Also, it will be observed that the forward or horizontal portion of the pocket P as seen in FIG. 10 has a somewhat greater longitudinal extent than does the rear or vertical portion, In other words, the center of curvature of the concave inner surface 16 and convex outer surface 17 is offset slightly toward the rear from the center of the circular outline of the pad.

The pad 15 comprises a core 18 of resilient, flexible cushioning material as seen in dashed lines in FIG. 9, and the core preferably comprises a porous foam material which is formed from discrete particles of foam material which are bonded together with a suitable adhesive binder during the molding operation, as further described below. Each of the inner concave surface 16 and outer convex surface 17 of the core has a sheet of fabric material 20, 21, respectively, lightly bonded thereto, The sheets 20, 21 smoothly overlie the surfaces of the core to present a neat appearance, and for this purpose, the sheets preferably comprise a porous knit fabric material which is adapted to smoothly conform to the surface of the core and stretch during any flexure of the core during the use or wearing of the pad. Fabrics of hydrophobic material, such as nylon, are preferred since they serve to conduct moisture and perspiration away from the wearer and thus are helpful in maintaining the skin free from irritation.

A narrow seam binding strip 23 is positioned to overlie the peripheral edge of the core 18 and two sheets 20, 21, the strip 23 being secured thereto by stitching 24 which passes through the two sheets and also through a portion of the peripheral edge of the core. The strip is overlapped along the rear peripheral edge, and th distal free ends of the strip form a pair of pliable binding elements or bands 26, 27 which extend tangentially from the peripheral edge in opposite directions, and which are adapted to be crossed about a body member such as the heel or elbow of the wearer and releasably engage one of the two conventional hook-type Velcro fasteners 31, 32 which are sewn or otherwise suitably secured to the outer convex surface 17 of the pad. Preferably, the strip 23 comprises a web of soft, fibrous fabric material of the type adapted to be engaged by the hook-type Velcro fasteners 31, 32, and the bands 26, 27 are formed by folding over the edges of the web and sewing the same together. Additional structural details of the pad 15 may be obtained by reference to the above noted copending application of Gaylord, Ser. No. 492.890.

Figure 1:
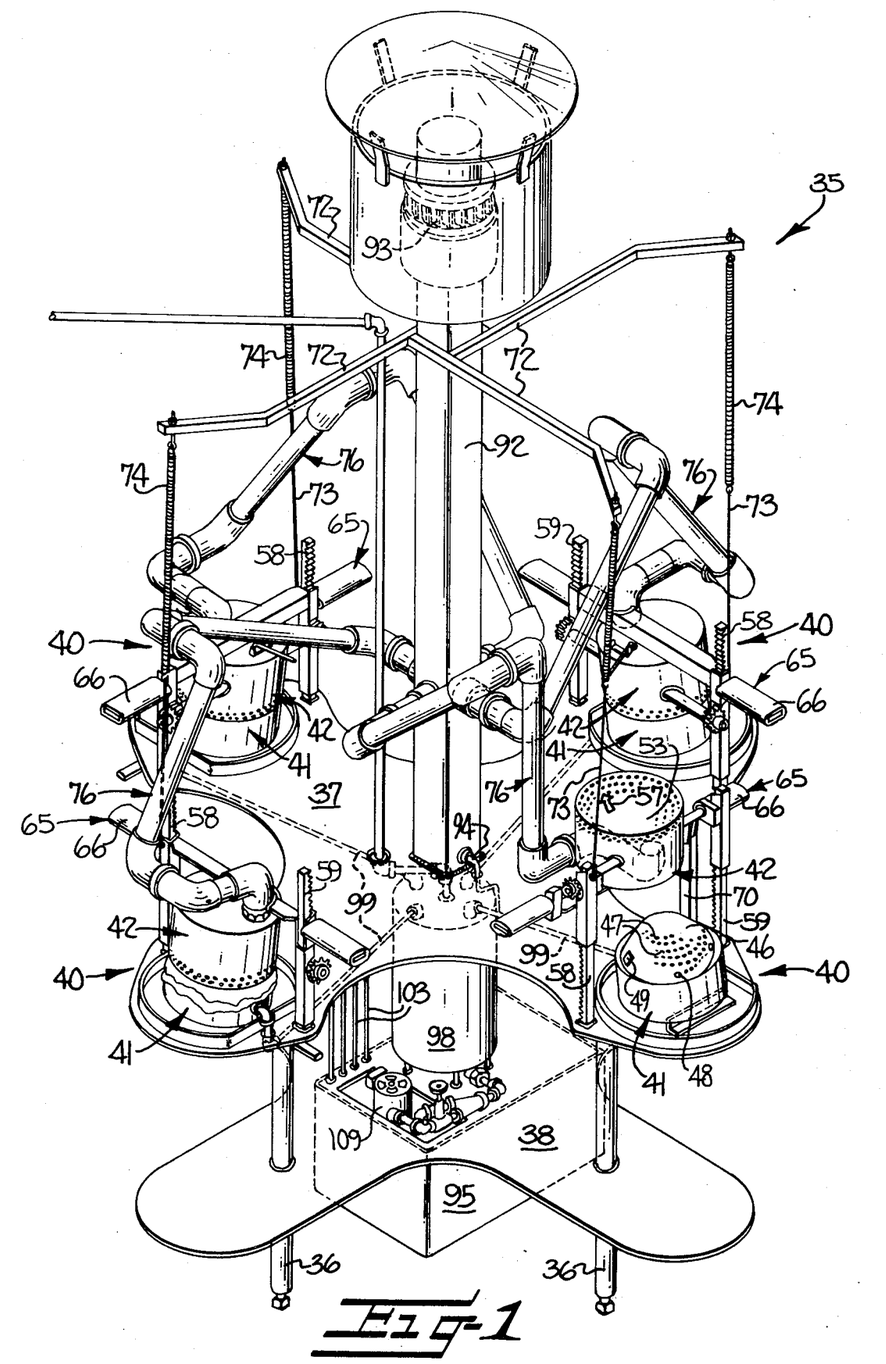
FIG. 1 is a perspective view of an apparatus embodying the features of the present invention.

The core 18 of the pad 15 may be molded in accordance with the present invention by an apparatus indicated generally at 35 in FIG. 1. More particularly, the apparatus 35 comprises a supporting frame which includes four pedestals 36, the pedestals in turn mounting upper and lower horizontal support platforms 37, 38, respectively. The apparatus includes four separate assembly stations 40 which are generally positioned on the upper support platform 37, with one station being positioned at each of the four corners of the apparatus. The assembly stations 40 are generally identical, and each comprises a male mold section or canister 41 fixedly mounted on the platform 37, and a female mold section or canister 42 carried by the platform 37 generally above the male canister.

Figure 4:
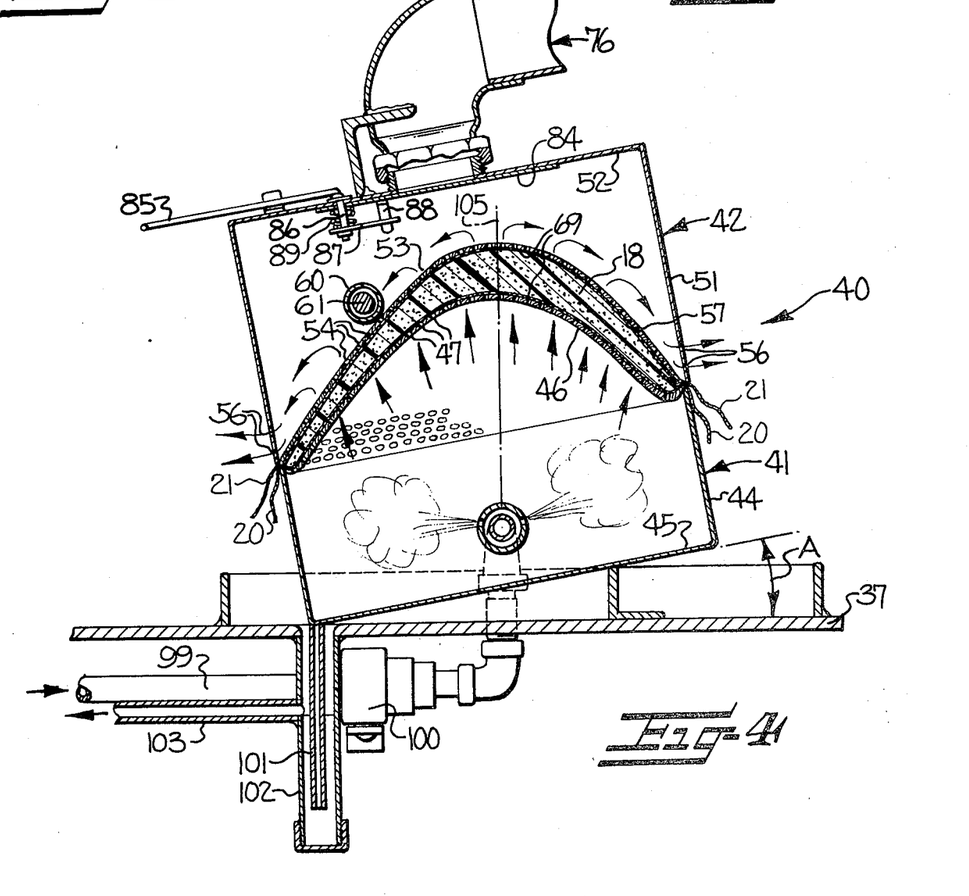
FIG. 4 is a sectional elevation view taken substantially along the line 4—4 of FIG. 3.

The male mold canister 41 comprises a cylindrical side wall 44, a bottom wall 45 closing the lower end of the side wall, and an upwardly facing generally convex mold surface 46 extending transversely across the upper end of the side wall. The canister is typically formed from stainless steel, and the convex mold surface 46 includes a plurality of relatively small perforations 47 substantially evenly distributed over the entire area thereof. Also, the surface includes a number of irregularities in the form of a pair of rounded protrusions 48, and a pair of square protrusions 49. As best seen in FIG. 4, the male canister is tilted at an angle A of about 10° for the purposes set forth below.

The female mold canister 42 comprises a generally cylindrical side wall 51 of a diameter generally conforming to that of the male canister, and further includes a bottom wall 52 closing the lower end of the side wall, and a generally concave mold surface 53 extending transversely across the upper end of the side wall 51. The concave mold surface 53 includes a plurality of perforations 54 substantially evenly distributed over the entire area thereof in a manner equivalent to the perforations 47 in the surface of the male canister 41. The surface 53 further fixedly mounts a small stainless steel wire or the like which is configured to define the outline of an arrow 57, note FIG. 1. In addition, the side wall 51 includes a plurality of closely spaced, relatively small perforations 56 adjacent the upper end thereof and communicating with the interior of the canister 42.

The female mold canister 42 is mounted on the frame generally above the male mold canister 41 and by an arrangement which permits the female mold to be pivoted about a substantially horizontal axis and moved downwardly along a substantially vertical path of travel onto the male canister. More particularly, the female canister 42 is mounted on the frame by an arrangement which includes a pair of vertical posts 58, 59, the posts being in the form of gear racks which are fixed to the platform 37 on opposite sides of the male canister 41. A sleeve 60 extends horizontally through and is fixed to the female canister 42, and a rod 61 is coaxially disposed within the sleeve 60 and is rotatably supported therein by the bushings 64. Each end of the rod 61 fixedly mounts a pinion 62 disposed in operative engagement with the gear of one of the posts 58, 59, the pinion and gears serving to prevent lateral shifting and binding of the female canister in its vertical movement along the posts 58, 59 as hereinafter further described. Also, an elongate collar 63 of rectangular cross-sectional configuration is slideably disposed over each of the posts 58 and 59, each collar 63 being rotatably carried at one end of the rod 61 by means of a bearing block 63a (which is fixed to the collar 63) and a bushing 64a.

A manually operable control arm 65 is mounted to the under surface of the bottom wall 52 of the female canister 42 and extends generally parallel to the rod 61. Each end of the arm 65 includes a manually grippable handle 66 and a collar segment 67 which is similar in configuration to that of the collars 63 on the rod 61. By this arrangement, the female canister 42 may be manually pivoted and translated between a non-operative or open position wherein the canisters are separated and the concave mold surface 53 faces upwardly (note FIG. 2), and an operative or closed position wherein the concave and convex mold surfaces are in a slightly spaced apart, face to face relationship (FIGS. 3 and 4) to define a mold cavity 69 therebetween which has a generally converging concavo-convex cross-sectional configuration. It will be noted that in the open position, each collar segment 67 is separated from the adjacent collar 63, and during pivotal movement the collar segments become coaxially aligned with the associated collar and thus become disposed about the associated post during the downward movement.

To support the weight of the female canister 42 in its open position, there is provided a vertically directed standard 70 which is mounted immediately adjacent the post 59 and in a position to engage the control arm 65. Also, the apparatus includes means for exerting a resilient lifting force on the female canister 42 to facilitate its movement by the operator. More particularly, the lifting means includes a framework of outwardly directed arms 72, with one arm 72 being positioned above each assembly station 40, and a wire or line 73, which includes a spring 74, interconnecting each arm 72 and the associated female canister 42. Thus a substantial portion of the weight of each female canister is carried by the framework of arms 72. While a single line 73 is shown in FIG. 1 interconnecting each arm and one of the collars 63 for clarity of illustration, it will be appreciated that a second line could be employed to interconnect the arm with the other collar.

Figure 7:
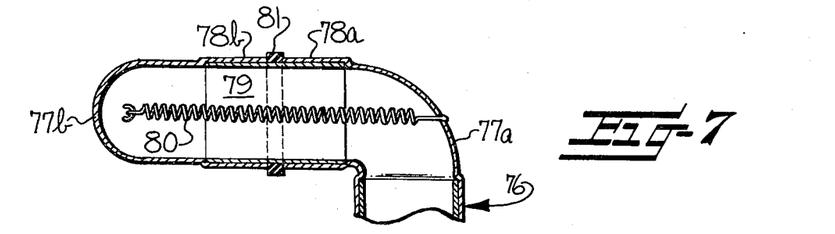
FIG. 7 is a fragmentary sectional plan view of a portion of the vacuum line as shown in FIG. 5.

A vacuum line 76 is operatively connected to an opening in the bottom wall 52 of each female canister 42 so as to communicate with the interior thereof, the vacuum line 76 comprising a number of interconnected tubular segments 77, such as two inch copper tubing, which are rotatably interconnected to permit the above described movement of the female canister. A representative joint is shown in FIG. 7, and comprises a first elbow segment 77a having an enlarged collar 78a at one end, an adjacent elbow segment 77b having an enlarged collar 78b disposed in opposing, coaxial relationship with the collar 78a of the first segment, and an internal sleeve 79 rotatably positioned within each of the collars to interconnect the same. A spring 80 is positioned within the joint to interconnect the two segments, and thereby serve to maintain their assembly. Also a resilient O-ring 81 is positioned on the outside of the sleeve 79 and intermediate the two collars to maintain the joint in a substantially sealed relationship. By placing a number of such joints in each vacuum line as seen in FIG. 1, the female mold canisters are free to move in the described manner.

Figure 5:
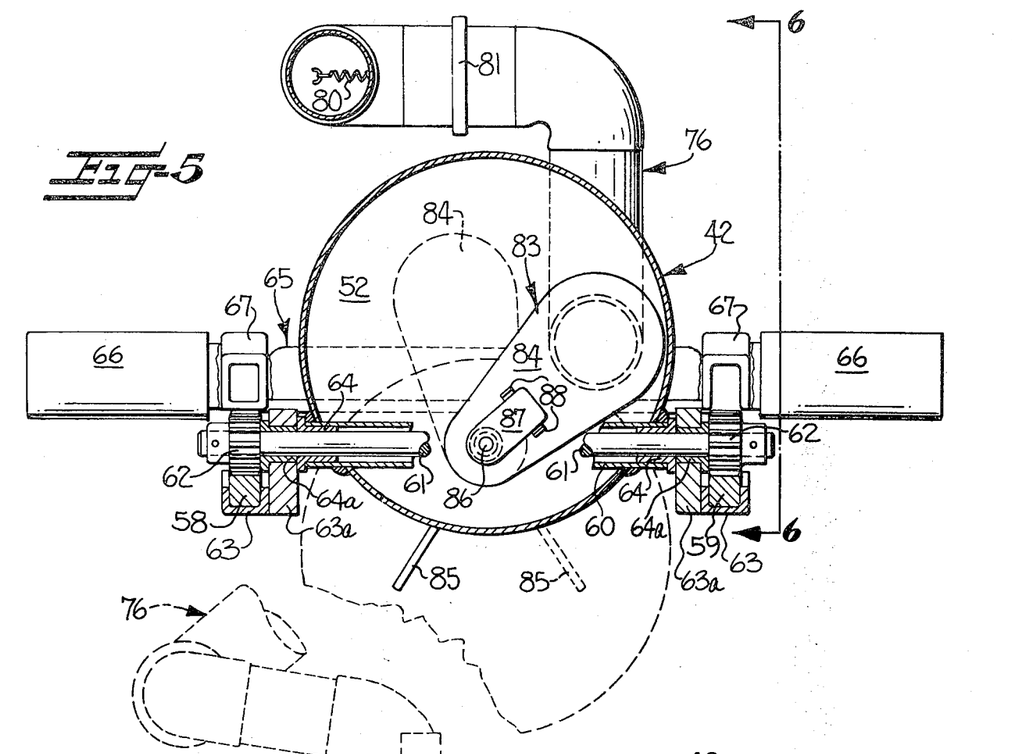
FIG. 5 is a sectional plan view taken substantially along the line 5—5 of FIG. 2.
Figure 6:
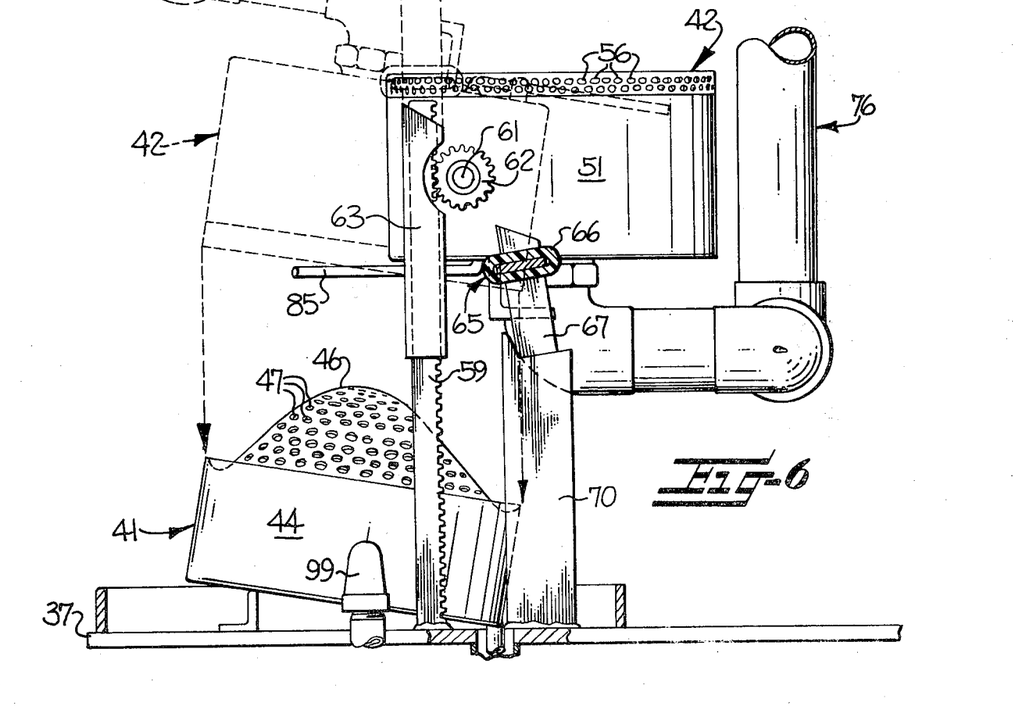
FIG. 6 is a side elevation view taken substantially along the line 6—6 of FIG. 5.

A valve 83 is associated with each vacuum line 76 to permit the operator to selectively draw a partial vacuum within each female canister 42. As best seen in FIGS. 4 and 5, the valve 83 comprises a pivotal plate 84 mounted within the female canister and immediately overlying the bottom wall 52. The plate 84 is pivotal between an open position as seen in dashed lines in FIG. 5, and a closed position as seen in solid lines and wherein the plate overlies the opening to the vacuum line 76. A lever 85 is mounted on the exterior of the canister and is operatively connected to the pivotal plate 84 such that movement of the lever by the operator acts to pivot the plate. More particularly, the interconnection between the plate and lever includes the vertical extension 86 and horizontal arm 87 which are fixedly connected to the lever 85, and a pair of shoulders 88 carried by the plate 84 which are adapted to be engaged by the arm 87. A spring 89 is interposed about the vertical extension 86 to bias the plate 84 against the bottom wall 52 and thereby assist in maintaining a sealed closure in the manner apparent from FIG. 4.

The remote end of each vacuum line is connected to a vacuum manifold 92 which comprises a vertically directed member positioned centrally within the apparatus and which also supports the above described framework of arms 72. An industrial fan 93 is mounted at the upper end of the manifold 92 for drawing a vacuum therewithin, the fan being driven by an electric motor of about one and one-half horsepower so as to be able to draw a vacuum of about one hundred inches of water. The lower end of the manifold includes a condensate drain line 94 leading to a sump 95 for removing any steam condensation as hereinafter further described.

Each assembly station 40 further comprises means for selectively introducing steam into the male mold canister 41. As best seen in FIG. 11, the system for supplying steam includes a suitable steam source 97 leading to a steam manifold 98, and an entry line 99 leading from the manifold 98 into each male canister. A manually operable valve 100 is positioned in each steam entry line to permit the operator to control the entry of the steam into the canister. The lowermost corner of the canister includes a condensate drain line 101, a steam trap 102, and a condensate line 103 leading to the sump. The sump 95 in turn includes a conventional float operated motor 109 and associated pump 110 for removing the steam condensate which is received from both the vacuum manifold 92 and the condensate lines 103.

As best seen in FIG. 4, the concave and convex mold surfaces 46, 53 define a common center line 105 when the canisters are in the operative position. In addition, it will be noted that the concave mold surface 53 has a somewhat shorter radius of curvature than that of the convex mold surface 46, to thereby result in the desired configuration of the mold which is suitable for molding a pad core 18 of generally converging concavo-convex cross-sectional configuration as employed in the above described pad 15. Thus the orientation of the center line 105 serves to offset the center of curvature of the inner surface 16 and outer surface 17 of the core 18, and results in the elongated front portion of the resulting pad 15 as described above.

It will be observed that the center line 105 of the mold surfaces extends substantially vertically by reason of the tilt of the canisters, and thus the vertical movement of the female canister 42 onto the male canister 41 is in a direction parallel to the center line 105. Further, the center line 105 of the mold surfaces will be seen to be disposed at an angle of about 10° from the central axis defined by the side walls of the male and female mold canisters, this angle corresponding to the tilt (angle A) of the canister.

Figure 2:
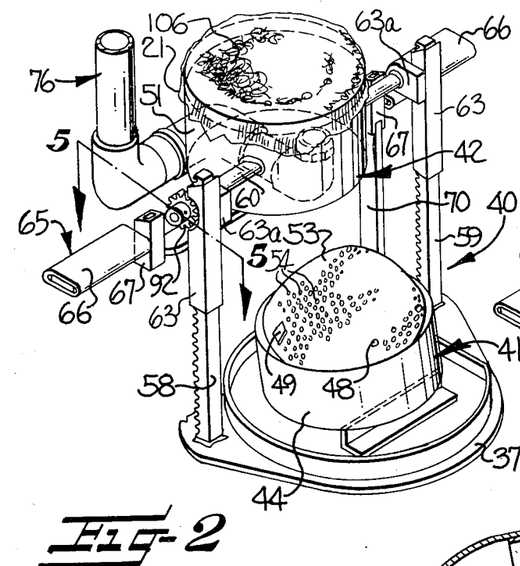
FIG. 2 is a fragmentary perspective view illustrating one assembly station of the apparatus shown in FIG. 1, and further showing the mold canisters in their open or non-operative position.

In operation, the female mold section 42 is initially positioned in its non-operative position as seen in FIG. 2, and the vacuum is introduced therein by opening the valve 83. A first fabric segment 21, such as a square of knit nylon fabric, is positioned upon the upwardly facing concave mold surface 53, and a second fabric segment 20 of like material is positioned upon the upwardly facing convex mold surface 46. In this regard, it has been found that initially wetting the fabric segments with water facilitates their smooth application upon the associated mold surface, and the surface tension and weight of the water serves to lightly adhere the fabric to the associated mold surface and thus maintain the fabric in the desired position. Also, the edges of the first fabric segment 21 may be lapped over the peripheral edge of the concave mold surface 53 so as to overlie the side wall 51 and be held thereto by the vacuum acting through the perforations 56. This arrangement tends to hold the first fabric segment snugly during the subsequent inverting of the female canister, and assures that the edges of the first fabric segment do not falll within the outline of the convex mold surface 46 during assembly as described below.

A predetermined amount of a relatively dry, particulate foam plastic material 106 (FIG. 2) having a heat curable adhesive mixed therewith is next positioned upon the concave mold surface 53 and over the first fabric segment 21. The foam plastic material typically comprises polyurethane foam ground to fine crumbs, and the adhesive typically comprises long polymer polyether urethane in a chlorinated solvent, and mixed in a one to five ratio by weight with the foam.

The deposited foam material 106 is preferably shaped by the operator into a generally dished or concave configuration such that the density of the center portion of the resulting molded product may be maintained at a desired low level, while the peripheral edge thereof has sufficient density to permit the subsequent sewing of the strip 23 or the like thereto. This shaping operation is done while the partial vacuum is maintained beneath the concave mold surface 53, such that the vacuum serves to maintain the desired distribution of the foam.

A sufficient amount of foam material 106 is deposited upon the concave mold surface to achieve an overall density of about three to four pounds per cubic foot in the resulting molded product, and in this regard, the density in various portions of the molded product may be varied by the above described shaping operation. For example, the central portion of the pad may have a relatively low density of about 2½ pounds per cubic foot to promote softness, while the peripheral edge may have a somewhat higher density of about 3½ to 4 pounds per cubic foot to provide sufficient integrity for the sewing of the strip thereto.

Figure 3:
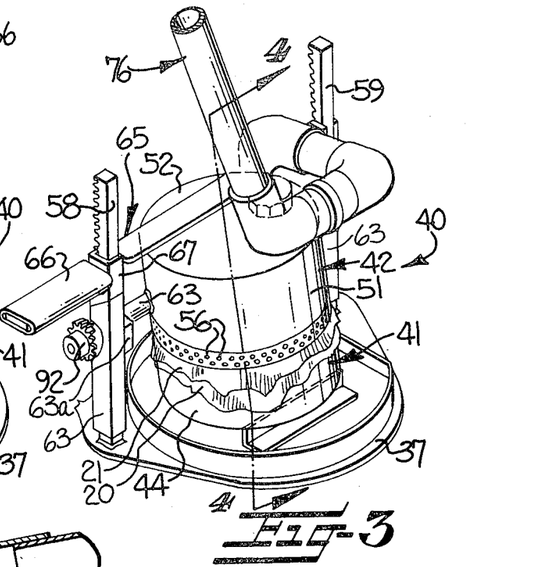
FIG. 3 is similar to FIG. 2 but illustrating the mold canisters in their closed or operative position.

The female mold canister 42 is then inverted by the operator pivoting the same about the horizontal axis of the rod 61, and the inverted female canister is lowered onto the male canister 41 to result in the operative closed mold position as seen in FIGS. 3 and 4. In this regard, it will be noted that the convex mold surface 46 moves vertically into the concave mold surface and along the center line 105 to thereby minimize any "dragging" of the foam material 106 into the center of the cavity. Also, the maintenance of the vacuum further serves to resist such movement. Thus the desired distribution of the foam material 106 is effectively maintained during the assembly of the mold canisters.

With the mold canisters closed, the operator closes the vacuum line valve 83, and opens the steam valve 100. The steam thus passes through the mold cavity 69 and into the female canister 42, and exhausts to the atmosphere through the perforations 56 in the side wall 51. The steam is maintained for a period of about four to five minutes to cure the adhesive, during which period the operator may move about the apparatus to service the other assembly stations 40. Upon completion of the curing operation, the female canister 42 is lifted and returned to its inverted position, and the molded intermediate product 107 as seen in FIGS. 8 and 9 is removed.

The molded product 107 is next placed into a dryer, such as a conventional commercial clothes dryer, to dry the water from the wetted fabric segments and any steam condensate within the molded core. The fabric edges are then trimmed, and the strip 23 sewn thereto. Finally, the "Velcro" fastening elements 31, 32 are sewn to the outer surface of the pad to result in the completed product 15. In this regard, it will be noted that the irregularities 48, 49 on the convex mold surface 46 result in slightly visible corresponding depressions 48a, 49a in the molded product 107, note FIG. 8. The rounded depressions 48a serve to indicate the placement of the overlapping portion of the strip 23, and the square depressions 49a indicate the placement of the fastening elements 31, 32 to thereby facilitate the final manufacturing operations. Also, the arrows 57 on the concave mold surface 53 rsults in a corresponding indentation in the form of an arrow 57a (FIG. 9) on the outer surface 17 of the pad, the arrow on the pad serving to advise the wearer which way to install the product. As illustrated, the arrow represents the rear of the pad when positioned on either the elbow or heel of the wearer.

In the drawings and specification, there has been set forth a preferred embodiment of the invention, and although specific terms are employed, they are used in a generic and descriptive sense only and not for purposes of limitation.

That which is claimed is:

1. A method of molding a protective pad adapted to be positioned on an elbow or heel of a patient and characterized by a generally arcuate cross-sectional configuration, and comprising the steps of depositing a predetermined amount of a relatively dry, particulate, foam polymeric material having a heat curable adhesive mixed therewith, in a predetermined concave distribution upon an upwardly facing concave mold surface having a plurality of perforations therethrough, drawing a partial vacuum beneath the concave mold surface such that the vacuum acts through the perforations to maintain the distribution of the foam material upon the concave mold surface, positioning the concave mold surface having the deposited foam material therein in spaced apart, face to face molding relationship with a convex mold surface such that the concave and convex mold surfaces define a mold cavity therebetween which is substantially filled with the foam material, and while maintaining the partial vacuum beneath the concave mold surface during the positioning step to maintain the distribution of the foam material in relation to the concave mold surface, heating the foam material while it is positioned in the mold cavity to thereby cure the adhesive and form a unitary molded product, and then separating the concave and comvex mold surfaces to release the resulting molded product.

2. The method as defined in claim 1 wherein said convex and concave mold surfaces define a common center line when positioned in said face to face relationship, and wherein the step of positioning the mold surfaces in face to face relationship includes translating one of the mold surfaces toward the other in a direction parallel to said center line to thereby avoid significant lateral movement of the molding material in relation to the concave mold surface.

3. The method as defined in claim 1 wherein the step of depositing the foam material upon the concave mold surface includes shaping the deposited material into a generally concave configuration while maintaining the partial vacuum beneath the concave mold surface, such that the density of the center portion of the resulting molded product may be maintained at a desired low level while a peripheral edge thereof has sufficient density to permit the subsequent sewing of a band thereto.

4. The method as defined in claim 1 comprising the further steps of
   positioning a first fabric segment over the concave mold surface prior to the positioning of the foam material thereon, and
   positioning a second fabric segment over the convex mold surface prior to positioning the concave and convex mold surfaces in face to face relationship, whereby the first and second fabric segments overlie the opposite faces of the resulting molded product and are adhered thereto by said adhesive.

5. The method as defined in claim 4 comprising the further steps of wetting each of the first and second fabric segments with water prior to positioning the same on the associated molding surface to thereby result in the fabric segments being initially lightly adhered to the associated mold surface and thus facilitate the smooth application of the fabric segments thereto.

6. The method as defined in claim 5 wherein the step of heating the foam material includes introducing steam into the mold cavity, and the method further comprises the subsequent step of drying the resulting molded product by subjecting the same to heated air to thereby remove the water from the wetted fabric segments and any steam condensate from within the molded foam.

7. A method of fabricating a protective pad adapted to be positioned on an elbow or heel of a patient and characterized by a generally circular outline and a generally arcuate cross-sectional configuration, and comprising the steps of
   positioning a first porous fabric segment upon an upwardly facing concave mold surface of circular outline and having a plurality of perforations therethrough,
   depositing a relativey dry, particulate, foam plastic material having a heat curable adhesive mixed therewith, in a predetermined distribution upon the upwardly facing concave mold surfaces and upon the first fabric segment,
   positioning a second porous fabric segment over an upwardly facing convex mold surface of circular outline and having a plurality of perforations therethrough,
   drawing a partial vacuum beneath the concave mold surface such that the vacuum acts through the associated perforations to maintain the positioning of the first fabric segment and the distribution of the foam material in relation to the concave mold surface,
   inverting the concave mold surface having the deposited foam material therein and linearly translating the same vertically downward into a spaced apart, face to face molding relationship with the convex mold surface such that the concave and convex mold surfaces define a mold cavity therebetween which is substantially filled with the foam material, and while maintaining the partial vacuum beneath the concave molding surface during the inverting and translating steps to maintain the first fabric segment and distribution of the foam material in relation to the concave mold surface, then
   introducing steam into the mold cavity by passing the same through the perforations in the concave and convex mold surfaces to thereby cure the adhesive in the foam material and for a unitary molded product, and then
   separating the concave and convex mold surfaces to release the resulting molded product.

8. The method as defined in claim 7 wherein the step of depositing the foam material upon the concave mold surface includes shaping the deposited foam material into a predetermined concave distribution while maintaining the partial vacuum beneath the concave mold surface.

9. The method as defined in claim 7 including the further step of terminating the partial vacuum prior to introducing steam into the mold cavity.

10. The method as defined in claim 7 comprising the further subsequent step of securing a fabric strip about the peripheral edge of the molded product so as to overlie the edges of the first and second fabric segments.

11. The method as defined in claim 10 comprising the further step of forming a pair of spaced apart binding bands which are attached to and extend tangentially from the peripheral edge of the molded product in opposite directions.

12. The method as defined in claim 11 comprising the further step of attaching a pair of fasteners which are adapted to releasably engage the binding bands, to the surface of the molded product.

13. The method as defined in claim 12 comprising the further step of forming visible indentations in the molded product during the curing of the molding material to indicate proper positioning of the binding bands and fasteners and to thereby facilitate subsequent attachment thereof to the molded product.

* * * * *

UNITED STATES PATENT AND TRADEMARK OFFICE
CERTIFICATE OF CORRECTION

PATENT NO. : 3,992,238

DATED : November 16, 1976

INVENTOR(S) : Herman S. Johns

It is certified that error appears in the above-identified patent and that said Letters Patent are hereby corrected as shown below:

```
Column 3, line 46,  "th" should be --the--.
Column 7, line 15,  "falll" should be --fall--.
Column 8, line 23,  "arrows" should be --arrow--;
Column 8, line 64,  "comvex" should be --convex--.
Column 9, line 29,  "steps" should be --step--;
Column 9, line 52,  "relativey" should be --relatively--.
Column 10, line 24, "for" should be --form--.
```

Signed and Sealed this

Eighth Day of February 1977

[SEAL]

Attest:

RUTH C. MASON
*Attesting Officer*

C. MARSHALL DANN
*Commissioner of Patents and Trademarks*